United States Patent
Gui et al.

(10) Patent No.: US 11,099,150 B1
(45) Date of Patent: Aug. 24, 2021

(54) METHOD FOR PREPARING RATIOMETRIC ELECTROCHEMICAL MIR3123 APTASENSOR BASED ON METAL-ORGANIC FRAMEWORK COMPOSITE

(71) Applicant: QINGDAO UNIVERSITY, Qingdao (CN)

(72) Inventors: Rijun Gui, Qingdao (CN); Yujiao Sun, Qingdao (CN); Hui Jin, Qingdao (CN); Xiaowen Jiang, Qingdao (CN)

(73) Assignee: QINGDAO UNIVERSITY, Qingdao (CN)

( * ) Notice: Subject to any disclaimer, the term of this patent is extended or adjusted under 35 U.S.C. 154(b) by 0 days.

(21) Appl. No.: 17/051,781

(22) PCT Filed: Aug. 30, 2019

(86) PCT No.: PCT/CN2019/103464
§ 371 (c)(1),
(2) Date: Oct. 30, 2020

(87) PCT Pub. No.: WO2021/035653
PCT Pub. Date: Mar. 4, 2021

(30) Foreign Application Priority Data

Aug. 27, 2019 (CN) .......................... 201910796313.5

(51) Int. Cl.
*G01N 27/327* (2006.01)
*G01N 27/30* (2006.01)
*G01N 27/48* (2006.01)
*C12Q 1/6825* (2018.01)
*C12Q 1/6886* (2018.01)
*B05D 1/00* (2006.01)

(52) U.S. Cl.
CPC .......... *G01N 27/3278* (2013.01); *B05D 1/00* (2013.01); *C12Q 1/6825* (2013.01); *C12Q 1/6886* (2013.01); *G01N 27/308* (2013.01); *G01N 27/3277* (2013.01); *G01N 27/48* (2013.01); *C12Q 2600/178* (2013.01)

(58) Field of Classification Search
None
See application file for complete search history.

(56) References Cited

FOREIGN PATENT DOCUMENTS

| CN | 102605042 A | 7/2012 |
|---|---|---|
| CN | 104531856 A | 4/2015 |
| CN | 104707569 A | 6/2015 |
| CN | 106124581 A | 11/2016 |
| CN | 108745404 A | 11/2018 |
| CN | 109239040 A | 1/2019 |
| CN | 109540991 A | 3/2019 |
| CN | 109602919 A | 4/2019 |
| CN | 110078034 A | 8/2019 |
| CN | 110146571 A | 8/2019 |

OTHER PUBLICATIONS

Jun Jin et al. Directly anchoring 2D NiCo metal-organic frameworks on few-layer black phosphorus for advanced lithium-ion batteries, Journal of Materials Chemistry A, 2019, pp. 783-790, 7.
Ming Li et al., Synthesis of a 2D phosphorus material in a MOF-based 2D nano-reactor, Chemical Science, 2018, pp. 5912-5918, 9.
Jundie Hu et al., Engineering black phosphorus to porous g-C3N4-metal-organic framework membrane: a platform for highly boosting photocatalytic performance, Journal of Materials Chemistry A, 2019, pp. 4408-4414, 7.
Jinqiong Xu et al., Electrostatic assembly of gold nanoparticles on black phosphorus nanosheets for electrochemical aptasensing of patulin, Microchim Acta, 2019, pp. 186-238.
Maryam Daneshpour et al., Simultaneous detection of gastric cancer-involved miR-106a and let-7a through a dual-signal-marked electrochemical nanobiosensor, Biosensors and Bioelectronics, 2018, pp. 197-205, 109.
Jisun Ki et al., Sensitive Plasmonic Detection of miR-10b in Biological Samples Using Enzyme-Assisted Target Recycling and Developed LSPR Probe, ACS Appl. Mater. Interfaces, 2019, pp. 18923-18929, 11.

*Primary Examiner* — Katherine D Salmon
(74) *Attorney, Agent, or Firm* — Bayramoglu Law Offices LLC

(57) ABSTRACT

A method for preparing a ratiometric electrochemical miR3123 aptasensor based on a copper-based metal-organic framework (Cu-MOF) composite doped with black phosphorus nanosheets (BPNSs) and thionine (TH) is provided. TH/Cu-MOF is prepared by reacting TH with Cu-MOF precursor, and BPNSs/TH/Cu-MOF is prepared by drop coating the BPNSs and drop coated onto an electrode. A ferrocene (Fc)-labeled single-stranded DNA aptamer is adsorbed on the BPNSs to prepare aptamer-BPNSs/TH/Cu-MOF. Target molecule miR3123 is bonded with the single-stranded DNA aptamer Fc-DNA, Fc-DNA is forced to escape from the BPNSs. Electrochemical signals of Fc are, therefore, weakened while TH signals are slightly affected. The ratiometric electrochemical miR3123 aptasensor is constructed by fitting a linear relationship between peak current intensity ratios $I_{Fc}/I_{TH}$ and concentrations of the miR3123.

1 Claim, 2 Drawing Sheets

METHOD FOR PREPARING RATIOMETRIC ELECTROCHEMICAL MIR3123 APTASENSOR BASED ON METAL-ORGANIC FRAMEWORK COMPOSITE

CROSS REFERENCE TO THE RELATED APPLICATIONS

This application is the national phase entry of International Application No. PCT/CN2019/103464, filed on Aug. 30, 2019, which is based upon and claims priority to Chinese Patent Application No. 201910796313.5, filed on Aug. 27, 2019, the entire contents of which are incorporated herein by reference.

TECHNICAL FIELD

The present invention relates to the technical field of preparation of metal organic framework composite materials and ratiometric electrochemical aptasensors, and more particularly, relates to a method for preparing a ratiometric electrochemical miR3123 aptasensor based on a copper-based metal-organic framework (Cu-MOF) nanocomposite co-doped with black phosphorus nanosheets and thionine. The aptasensor prepared by the method can be used for a highly sensitive, highly selective, and quantitative detection of the miR3123 in biomedical samples.

BACKGROUND

MicroRNAs, abbreviated as miRNAs, are a class of non-coding single-stranded RNA molecules encoded by endogenous genes with a length of approximately 22 nucleotides. In the process of cell differentiation and biological development, miRNAs play a role in regulating post-transcriptional gene expression in plants and animals. With their remarkable functions, miRNAs have attracted a lot of interest of individuals working in science and technology. Researchers have found that the gene regulation of small RNA plays an important role in the development of tumors, heart disease and nervous system diseases. Small RNA is, therefore, considered as a new biomarker for research on disease diagnosis.

Current methods for detecting small RNA include fluorescence quenching, isothermal exponential amplification, electrochemiluminescence, and real-time polymerase chain reaction platforms. miR3123 is a 17-nucleotide microRNA, which shows obvious expression changes in early gastric cancer and can be used as a potential biomarker for early diagnosis of gastric cancer. Quantitative detection of the miR3123 in humans is helpful for the early diagnosis and treatment of gastric cancer.

Daneshpour et al. designed a dual-signal-marked electrochemical nanobiosensor for the detection of a gastric cancer-related marker miR-106a (Maryam Daneshpour, Behzad Karimi, Kobra Omidfar. Simultaneous detection of gastric cancer-involved miR-106a and let-7a through a dual-signal-marked electrochemical nanobiosensor. *Biosensors and Bioelectronics,* 2018, 109, 197-205). Ki et al. developed a localized surface plasmon resonance sensor based on an enzyme-assisted target recycling system for the detection of a gastric cancer-related marker miR-10b (Jisun Ki, Hyo young Lee, Hye Young Son, Yong-Min Huh, Seungjoo Haam. Sensitive plasmonic detection of miR-10b in biological samples using enzyme-assisted target recycling and developed LSPR probe. *ACS Appl. Mater. Interfaces,* 2019, 11, 18923-18929). LIU Hanshao et al. discloses a method for performing reverse transcription and real-time quantitative PCR reaction on a gastric cancer biomarker miR-378, and using U6snRNA as an internal reference to calculate the relative quantitative PCR value of the miR-378 (LIU Hanshao; MENG Xianxin; ZHANG Wei; ZHANG Chunxiu; XIAO Huasheng. Application of miR-378 biomarker in detection and diagnosis of gastric cancer. China National Invention Patent Publication No. CN102605042A). WANG Zhenning et al. discloses a kit for a gastric cancer process related molecular marker miR-1258, which is used for the early evaluation of prognosis for gastric cancer after operation (WANG Zhenning; SONG Yongxi; ZHOU Xin; HUANG Xuanzhang; GAO Peng; SUN Jingxu; CHEN Xiaowan. Gastric cancer process and prognosis related molecular marker miR-1258. China National Invention Patent Publication No. CN104531856A).

Although international works relating to the detection of small RNA related markers of gastric cancer have been published in China and other countries, no Chinese or overseas literature or patent documents related to the quantitative detection of miR3123 have been published. Accordingly, the present invention provides a method for quantitative detection of gastric cancer-related marker miR3123, and includes a method for preparing a ratiometric electrochemical miR3123 aptasensor based on a copper-based metal-organic framework (Cu-MOF) nanocomposite codoped with black phosphorus nanosheets (BPNSs) and thionine (TH).

A TH/Cu-MOF composite is prepared by reacting the TH with a Cu-MOF precursor. A BPNSs dispersion is drop coated on the composite to prepare a BPNSs/TH/Cu-MOF composite. The composite is drop coated on the surface of a bare glassy carbon electrode, a ferrocene (Fc)-labeled single-stranded DNA aptamer is adsorbed on the BPNSs to prepare an aptamer-BPNSs/TH/Cu-MOF nanocomposite. Target molecule miR3123 specifically binds to the single-stranded DNA aptamer to cause Fc-DNA to escape from BPNSs and away from the surface of the electrode, leading to weakened electrochemical signals of Fc. The influence on electrochemical signals of the TH is negligible during this process. Therefore, using the TH as a reference and the Fc as a signal response unit, a ratio electrochemical miR3123 aptamer sensor is constructed by fitting a linear relationship between redox peak current intensity ratios $I_{Fc}/I_{TH}$ and concentrations of the miR3123. Until this writing, there have been no published works, patent documents or reports of Cu-MOF nanocomposites codoped with BPNSs and TH, and ratiometric electrochemical aptasensors for the quantitative detection of miR3123 in Chinese and/or overseas literature.

SUMMARY

The objective of the present invention is to overcome the shortcomings of the prior art described above, and to provide a method for preparing a ratiometric electrochemical miR3123 aptasensor based on a Cu-MOF nanocomposite codoped with BPNSs and TH with simple method, low cost, high sensitivity and excellent selectivity.

To achieve the above-mentioned objective, the present invention provides a method for preparing a ratiometric electrochemical miR3123 aptasensor based on a Cu-MOF nanocomposite codoped with BPNSs and TH, including the following steps:

(1) preparation of a TH/Cu-MOF composite: separately weighing 4 mg of copper nitrate trihydrate, 10 μL of trifluoroacetic acid and 10 mg of polyvinylpyrrolidone (PVP) and adding into 12 mL of a mixed solvent containing 9 mL of N,N-dimethylformamide and 3 mL of ethanol, and stirring uniformly to form a mixture A; separately weighing 4 mg of 4,4',4",4"'-(porphine-5,10,15,20-tetrayl)tetrakis (benzoic acid) and 4 mg of TH and adding to a mixed solvent containing 3 mL of N,N-dimethylformamide and 1 mL of ethanol, and stirring uniformly to form a mixture B; adding the mixture A dropwise to the mixture B, stirring, and sonicating for 10 min; heating an A-B mixture to 80° C. and reacting for 3 h; centrifuging a resulting product solution for 10 min at 8,000 rpm, washing with ethanol and distilled water, and drying to obtain the TH/Cu-MOF composite, and dispersing the TH/Cu-MOF composite in ethanol for later use;

(2) preparation of a BPNSs/TH/Cu-MOF composite: weighing 15 mg of black phosphorus bulk crystals and adding into 30 mL of 1-methyl-2-pyrrolidone, sonicating in an ultrasonic cleaner for 6 h, and then transferring to a probe-type ultrasonic generator and sonicating for 4 h; centrifuging a sonicated dispersion for 20 min at 10,000 rpm to remove larger-size products, and centrifuging an upper dispersion for 20 min at 3,500 rpm to obtain a BPNSs dispersion; adding the BPNSs dispersion dropwise to a TH/Cu-MOF composite dispersion, sonicating for 1 h under a stirring, and then centrifuging for 15 min at 8,000 rpm to prepare the BPNSs/TH/Cu-MOF composite dispersion for later use;

(3) preparation of an aptamer-BPNSs/TH/Cu-MOF nanocomposite: adding a cross-linking agent Nafion dropwise on the surface of a polished bare glassy carbon electrode, and then drop coating the BPNSs/TH/Cu-MOF composite dispersion to form a glassy carbon electrode modified by the composite; immersing the modified electrode in phosphate buffered saline (PBS) containing 1-10 μM of miR3123-corresponding single-stranded DNA aptamer Fc-DNA, and incubating for 2 h at 37° C.; then taking out the electrode, and drying naturally to prepare the aptamer-BPNSs/TH/Cu-MOF nanocomposite on the surface of the electrode; and (4) using an aptamer-BPNSs/TH/Cu-MOF nanocomposite modified glassy carbon electrode as a working electrode and placing in a three-electrode system of an electrochemical workstation; using the PBS as an electrolyte, adding a predetermined amount of miR3123 to determine electrochemical square wave voltammetry curves at different concentrations of the miR3123; using redox peak current intensities of the TH and the Fc as a reference signal and a response signal, respectively, fitting a linear relationship between peak current intensity ratios $I_{Fc}/I_{TH}$ and concentrations of the miR3123 to construct a ratiometric electrochemical aptasensor for quantitative detection of the miR3123, in which a linear detection concentration of the miR3123 is 1 nM-10 μM, and a detection limit is 1-5 nM.

The advantages of the present invention are as follows: a method for preparing a ratiometric electrochemical miR3123 aptasensor based on a Cu-MOF nanocomposite codoped with BPNSs and TH is provided. First, the TH and a Cu-MOF precursor are reacted together to prepare a TH/Cu-MOF composite; freshly prepared BPNSs dispersion is drop coated on the TH/Cu-MOF composite to prepare a BPNSs/TH/Cu-MOF composite; the composite is drop coated on the surface of a bare glassy carbon electrode to construct a composite-modified glassy carbon electrode. An Fc-labeled single-stranded DNA aptamer is enriched on the BPNSs by adsorption to prepare an aptamer-BPNSs/TH/Cu-MOF nanocomposite. Target molecule miR3123 specifically binds to single-stranded DNA aptamer Fc-DNA to cause Fc-DNA to escape from BPNSs, that is, Fc is far from the surface of the electrode, leading to weakened electrochemical signals of Fc; the influence on electrochemical signals of TH is negligible during this process. Accordingly, using the TH as a reference and the Fc as a signal response unit, a ratio electrochemical miR3123 aptamer sensor is constructed by fitting a linear relationship between redox peak current intensity ratios $I_{Fc}/I_{TH}$ and concentrations of the miR3123. Compared with the prior art, the method has the advantages of simple and convenient operation, strong anti-interference capability of the ratiometric electrochemical signals, high detection sensitivity and excellent selectivity, and can be used as a novel ratiometric electrochemical sensor for high-sensitivity and high-selectivity quantitative detection of miR3123 in biomedical samples.

DETAILED DESCRIPTION OF THE EMBODIMENTS

The present invention will be described in detail below with reference to the drawings.

Embodiment 1

Figure 1:
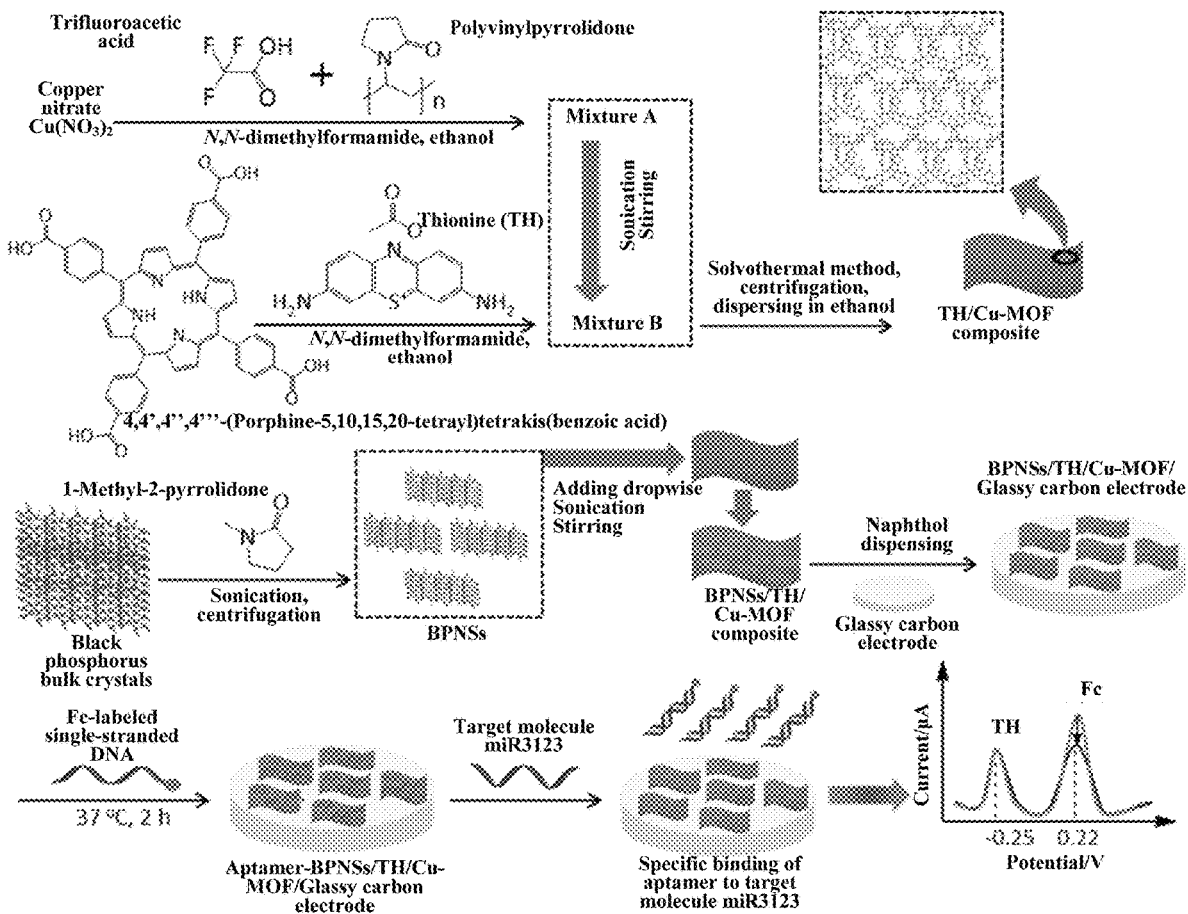
FIG. 1 is a schematic diagram of a preparation of a ratiometric electrochemical miR3123 aptasensor based on a Cu-MOF nanocomposite codoped with BPNSs and TH and a detection of miR3123 according to present invention.

A method for preparing a ratiometric electrochemical miR3123 aptasensor based on a Cu-MOF nanocomposite codoped with BPNSs and TH according to embodiment 1 is provided. The schematic diagram of the preparation process and the principle of miR3123 detection thereof are shown in FIG. 1. The specific process steps are as follows:

Preparation of a TH/Cu-MOF composite: 4 mg of copper nitrate trihydrate, 10 μL of trifluoroacetic acid and 10 mg of polyvinylpyrrolidone (PVP) were separately weighed and added into 12 mL of a mixed solvent containing 9 mL of N,N-dimethylformamide and 3 mL of ethanol, and stirred uniformly to form a mixture A. 4 mg of 4,4',4",4"'-(porphine-5,10,15,20-tetrayl)tetrakis(benzoic acid) and 4 mg of TH were separately weighed and added to a mixed solvent containing 3 mL of N,N-dimethylformamide and 1 mL of ethanol, and stirred uniformly to form a mixture B. The mixture A was added dropwise to the mixture B, stirred, and sonicated for 10 min; an A-B mixture was heated to 80° C. and reacted for 3 h. A resulting product solution was centrifuged for 10 min at 8,000 rpm, washed with ethanol and distilled water, and dried to obtain the TH/Cu-MOF composite, and the composite was dispersed in ethanol for later use.

Preparation of a BPNSs/TH/Cu-MOF composite: 15 mg of black phosphorus bulk crystals was weighed and added into 30 mL of 1-methyl-2-pyrrolidone, sonicated in an ultrasonic cleaner for 6 h, and then transferred to a probe-type ultrasonic generator and sonicated for 4 h. A sonicated dispersion was centrifuged for 20 min at 10,000 rpm to remove larger-size products, and the upper dispersion was centrifuged for 20 min at 3,500 rpm to obtain a BPNSs dispersion. The BPNSs dispersion was added dropwise to a TH/Cu-MOF composite dispersion, sonicated for 1 h under stirring, and then centrifuged for 15 min at 8,000 rpm to prepare the BPNSs/TH/Cu-MOF composite dispersion for later use.

Preparation of an aptamer-BPNSs/TH/Cu-MOF nanocomposite: Cross-linking agent Nafion was added dropwise on the surface of a polished bare glassy carbon electrode, and then the BPNSs/TH/Cu-MOF composite dispersion was drop coated to form a glassy carbon electrode modified by the composite. The modified electrode was immersed in phosphate buffered saline (PBS) containing 2 μM of miR3123-corresponding single-stranded DNA aptamer Fc-DNA, and incubated for 2 h at 37° C.; then the electrode was taken out, and the aptamer-BPNSs/TH/Cu-MOF nanocomposite was prepared on the surface of the electrode after drying naturally.

Figure 2A:
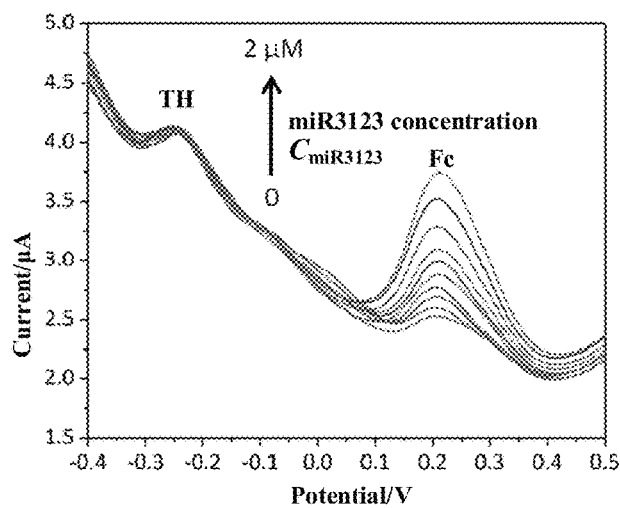
FIG. 2A is a diagram of electrochemical square wave voltammetry curves corresponding to a ratiometric electrochemical aptasensor system at different concentrations of the miR3123.
Figure 2B:
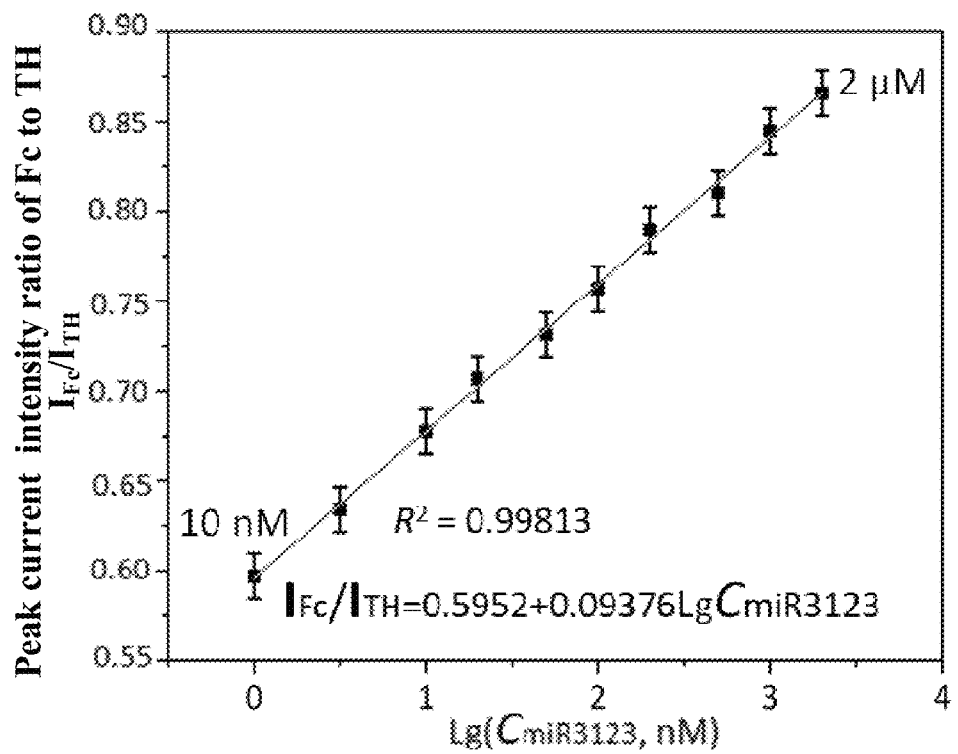
FIG. 2B is a diagram of a linear relationship between different ratio values $I_{Fc}/I_{TH}$ and concentrations of the miR3123 based on redox peak current intensity ratios $I_{Fc}/I_{TH}$ of Fc to TH corresponding to the concentrations of the miR3123.

An aptamer-BPNSs/TH/Cu-MOF nanocomposite modified glassy carbon electrode was used as a working electrode and placed in a three-electrode system of an electrochemical workstation; PBS was used as an electrolyte, and a predetermined amount of miR3123 was added to determine electrochemical square wave voltammetry curves at different concentrations of the miR3123 (as shown in FIG. 2A); redox peak current intensities of the TH and the Fc were used as a reference signal and a response signal, respectively, a linear relationship between the ratio of two peak current intensities $I_{Fc}/I_{TH}$ and concentrations of the miR3123 was fitted (as shown in FIG. 2B) to construct a ratiometric electrochemical aptasensor for quantitative detection of the miR3123. A linear detection concentration of the miR3123 was 10 nM-2 μM, and a detection limit was 2 nM.

Embodiment 2

A method for preparing a ratiometric electrochemical aptasensor based on a Cu-MOF nanocomposite codoped with BPNSs and TH according to embodiment 1 is provided. The schematic diagram of the preparation process and the principle of miR3123 detection thereof, the process steps for the preparation of the TH/Cu-MOF and the BPNSs/TH/Cu-MOF composite are the same as those in embodiment 1. Other specific process steps are as follows:

A cross-linking agent Nafion was added dropwise on the surface of a polished bare glassy carbon electrode, and then the BPNSs/TH/Cu-MOF composite dispersion was drop coated to form a glassy carbon electrode modified by the composite. The modified electrode was immersed in phosphate buffered saline (PBS) containing 5 μM of miR3123-corresponding single-stranded DNA aptamer Fc-DNA, and incubated for 2 h at 37° C.; then the electrode was taken out, and an aptamer-BPNSs/TH/Cu-MOF nanocomposite was prepared on the surface of the electrode after drying naturally.

An aptamer-BPNSs/TH/Cu-MOF nanocomposite modified glassy carbon electrode was used as a working electrode and placed in a three-electrode system of an electrochemical workstation; PBS was used as an electrolyte, and a predetermined amount of miR3123 was added to determine electrochemical square wave voltammetry curves at different concentrations of the miR3123; redox peak current intensities of the TH and the Fc were used as a reference signal and a response signal, respectively, a linear relationship between the ratio of two peak current intensities $I_{Fc}/I_{TH}$ and concentrations of the miR3123 was fitted to construct a ratiometric electrochemical aptasensor for quantitative detection of the miR3123. A linear detection concentration of the miR3123 was 10 nM-10 μM, and a detection limit was 5 nM.

Embodiment 3

A method for preparing a ratiometric electrochemical aptasensor based on a Cu-MOF nanocomposite codoped with BPNSs and TH according to embodiment 3 is provided. The schematic diagram of the preparation process and the principle of miR3123 detection thereof, the process steps for the preparation of the TH/Cu-MOF and the BPNSs/TH/Cu-MOF composite are the same as those in embodiment 1. Other specific process steps are as follows:

A cross-linking agent Nafion was added dropwise on the surface of a polished bare glassy carbon electrode, and then the BPNSs/TH/Cu-MOF composite dispersion was drop coated to form a glassy carbon electrode modified by the composite. The modified electrode was immersed in phosphate buffered saline (PBS) containing 8 μM of miR3123-corresponding single-stranded DNA aptamer Fc-DNA, and incubated for 2 h at 37° C. Then the electrode was taken out, and an aptamer-BPNSs/TH/Cu-MOF nanocomposite was prepared on the surface of the electrode after drying naturally.

An aptamer-BPNSs/TH/Cu-MOF nanocomposite modified glassy carbon electrode was used as a working electrode and placed in a three-electrode system of an electrochemical workstation. PBS was used as an electrolyte, and a predetermined amount of miR3123 was added to determine electrochemical square wave voltammetry curves at different concentrations of the miR3123; redox peak current intensities of the TH and the Fc were used as a reference signal and a response signal, respectively, a linear relationship between the ratio of two peak current intensities $I_{Fc}/I_{TH}$ and concentrations of the miR3123 was fitted to construct a ratiometric electrochemical aptasensor for quantitative detection of the miR3123. A linear detection concentration of the miR3123 was 1 nM-1 μM, and a detection limit was 1 nM.

The foregoing descriptions are merely preferred embodiments of the present invention. It should be noted that several variations and modifications can be made by those skilled in the art without departing from the principle of the present invention and should also fall within the protection scope of the invention.

What is claimed is:

1. A method for preparing a ratiometric electrochemical miR3123 aptasensor based on a metal-organic framework (MOF) composite comprising the following steps:
    (1) preparation of a thionine (TH)/copper-based metal-organic framework (Cu-MOF) composite: separately weighing 4 mg of copper nitrate trihydrate, 10 μL of trifluoroacetic acid and 10 mg of polyvinylpyrrolidone (PVP) and adding the copper nitrate trihydrate, the trifluoroacetic acid and the PVP into 12 mL of a first mixed solvent containing 9 mL of N,N-dimethylformamide and 3 mL of ethanol for a uniform stirring to form a first mixture; separately weighing 4 mg of 4,4',4",4"'-(porphine-5,10,15,20-tetrayl)tetrakis(benzoic acid) and 4 mg of TH and adding the 4,4',4",4"'-(porphine-5,10,15,20-tetrayl)tetrakis(benzoic acid) and the TH to a second mixed solvent containing 3 mL of N,N-dimethylformamide and 1 mL of ethanol for a uniform stirring to form a second mixture; adding the first mixture dropwise to the second mixture to obtain a third mixture for stirring and sonicating for 10 min; heating the third mixture to 80° C. and reacting for 3 h to obtain a first resulting product solution; centrifuging the first resulting product solution for 10 min at 8,000 rpm to obtain a second resulting product solution, washing the second resulting product solution with ethanol and distilled water to obtain a third resulting product solution, and drying the third resulting product solution to obtain the TH/Cu-MOF composite, and the TH/Cu-MOF composite is dispersed in ethanol to obtain a TH/Cu-MOF composite dispersion for later use;

(2) preparation of a black phosphorus nanosheets (BPNSs)/TH/Cu-MOF composite: weighing 15 mg of black phosphorus bulk crystals and adding the black phosphorus bulk crystals into 30 mL of 1-methyl-2-pyrrolidone to obtain a fourth mixture, sonicating the fourth mixture in an ultrasonic cleaner for 6 h, and then transferring the fourth mixture to a probe-type ultrasonic generator and sonicating for 4 h; centrifuging the fourth mixture for 20 min at 10,000 rpm to remove larger-size products from the fourth mixture to obtain an upper dispersion, and centrifuging the upper dispersion for 20 min at 3,500 rpm to obtain a BPNSs dispersion; adding the BPNSs dispersion dropwise to the TH/Cu-MOF composite dispersion to obtain a fifth mixture, sonicating the fifth mixture for 1 h under a stirring, and then centrifuging the fifth mixture for 15 min at 8,000 rpm to prepare a BPNSs/TH/Cu-MOF composite dispersion for later use;

(3) preparation of an aptamer-BPNSs/TH/Cu-MOF nanocomposite: adding a cross-linking agent Nafion dropwise on a surface of a polished bare glassy carbon electrode to obtain a first resulting carbon electrode, and then drop coating the BPNSs/TH/Cu-MOF composite dispersion on the first resulting carbon electrode to form a second resulting glassy carbon electrode, wherein the second resulting glassy carbon electrode is modified by the BPNSs/TH/Cu-MOF composite; immersing the second resulting glassy carbon electrode in phosphate buffered saline (PBS) containing 1-10 μM of miR3123-corresponding single-stranded DNA aptamer Fc-DNA to obtain a sixth mixture, and incubating the sixth mixture for 2 h at 37° C. to obtain a third resulting glassy carbon electrode; then taking out the third resulting glassy carbon electrode, and drying the third resulting glassy carbon electrode naturally to prepare the aptamer-BPNSs/TH/Cu-MOF nanocomposite on a surface of the third resulting glassy carbon electrode; and (4) using an aptamer-BPNSs/TH/Cu-MOF nanocomposite modified glassy carbon electrode as a working electrode and placing the aptamer-BPNSs/TH/Cu-MOF nanocomposite modified glassy carbon electrode in a three-electrode system of an electrochemical workstation; using PBS as an electrolyte, adding a predetermined amount of miR3123 to determine electrochemical square wave voltammetry curves at different concentrations of the miR3123; using a redox peak current intensity of the TH as a reference signal, and using a redox peak current intensity of Fc as a response signal, respectively, fitting a linear relationship between peak current intensity ratios $I_{Fc}/I_{TH}$ and the concentrations of the miR3123 to construct a ratiometric electrochemical aptasensor for a quantitative detection of the miR3123, wherein a linear detection concentration of the miR3123 is 1 nM-10 μM, and a detection limit is 1-5 nM.

* * * * *